United States Patent
Dolev (10) Patent No.: US 9,301,775 B2
(45) Date of Patent: *Apr. 5, 2016

(54) FINGERNAIL DRILL

(71) Applicant: Moshe Dolev, Udim (IL)

(72) Inventor: Moshe Dolev, Udim (IL)

(\*) Notice: Subject to any disclaimer, the term of this patent is extended or adjusted under 35 U.S.C. 154(b) by 64 days.

This patent is subject to a terminal disclaimer.

(21) Appl. No.: 13/905,360

(22) Filed: May 30, 2013

(65) Prior Publication Data

US 2014/0358171 A1    Dec. 4, 2014

(51) Int. Cl.
| | | |
|---|---|---|
| *A61B 17/3209* | (2006.01) | |
| *A61B 17/16* | (2006.01) | |
| *A61B 17/54* | (2006.01) | |
| *A61M 5/00* | (2006.01) | |

(52) U.S. Cl.
CPC ......... *A61B 17/3209* (2013.01); *A61B 17/1604* (2013.01); *A61B 17/1686* (2013.01); *A61B 17/54* (2013.01); *A61M 5/00* (2013.01)

(58) Field of Classification Search
CPC ............. A61B 17/32002; A61B 2017/320032; A61B 17/3209; A61B 17/1615; A61B 17/1686
USPC ............................ 606/80, 167, 172, 180–183; 408/227–230; 132/73, 73.5, 73.6, 75.4, 132/75.6, 75.8, 76.4
See application file for complete search history.

(56) References Cited

U.S. PATENT DOCUMENTS

| | | | | |
|---|---|---|---|---|
| 2,801,633 A | * | 8/1957 | Ehrlich | 606/181 |
| 3,766,923 A | | 10/1973 | Boretos | |
| 4,616,649 A | * | 10/1986 | Burns | 606/182 |
| 5,395,387 A | * | 3/1995 | Burns | 606/181 |
| 5,490,938 A | * | 2/1996 | Sawan et al. | 210/651 |
| 5,645,554 A | | 7/1997 | Hugh | |
| 6,227,774 B1 | * | 5/2001 | Haughton et al. | 408/225 |
| 2002/0172923 A1 | * | 11/2002 | Strong et al. | 433/165 |
| 2006/0225757 A1 | * | 10/2006 | Jamison, Jr. | 132/73.6 |
| 2009/0306696 A1 | * | 12/2009 | Doi | 606/182 |
| 2010/0145373 A1 | * | 6/2010 | Alon | 606/169 |

FOREIGN PATENT DOCUMENTS

| | | |
|---|---|---|
| DE | 202011003971 | 5/2011 |
| GB | 1080673 | 8/1967 |
| WO | 2006/104600 | 10/2006 |

OTHER PUBLICATIONS

PCT Search Report PCT/US2014/018502, Apr. 24, 2014.

\* cited by examiner

*Primary Examiner* — Thomas McEvoy
(74) *Attorney, Agent, or Firm* — Dekel Patent Ltd; David Klein (57) ABSTRACT

A fingernail drill has a drill bit and a tip which is capable of drilling through a thickness of a fingernail. The tip extends longitudinally outwards from an abutment integrally formed with the drill bit, and the drill cannot drill past the abutment. The distance from the abutment to a distal end of the tip is such that the drill can drill through the thickness of the fingernail but cannot damage tissue under the fingernail. A kit is provided that includes the fingernail drill and a dispenser for dispensing a substance through a hole drilled by the fingernail drill.

10 Claims, 8 Drawing Sheets

FINGERNAIL DRILL

CROSS-REFERENCE TO RELATED APPLICATIONS

This application is a continuation-in-part of U.S. patent application Ser. No. 13/769,394 filed 18 Feb. 2013, which is incorporated herein by reference.

FIELD OF THE INVENTION

The present invention relates generally to a hand drill for relieving swelling underneath a fingernail ("fingernail" includes toenail), and more specifically to a hand drill that ensures proper puncturing of the nail while preventing any possible encroachment of the drill into the tissue under the nail.

BACKGROUND OF THE INVENTION

A common type of human injury occurs when a finger or toe is smashed, such as by an inadvertent hammer blow, door slam, etc. A result of these accidents is a very painful bruise and swelling under the nail, called a subungual hematoma.

In order to relieve the swelling under the nail, the nail is perforated to permit blood or other body fluids to ooze out to relieve pressure. By directing the pooling blood out of the restricted space under the nail, several beneficial results occur. First, the pressure under the nail is relieved so that the swelling and throbbing pain is reduced. Second, discoloration of the nail is lessened. Finally, premature loss of the nail is avoided. In the prior art, the nail has been perforated by burning the nail with a red-hot wire, or by puncturing with the tip of a hypodermic needle. A problem is lack of control: the delicate tissue under the nail can also be perforated, which can lead to additional pain and worsening of the wound.

Nail boring devices (called trephinators) are known in the art. U.S. Pat. No. 6,015,418 and US Patent Application 2006/0225757 describe hand drills for drilling a pressure-relief hole in the nail (2006/0225757 also has an electrically powered drill). However, there is no provision of making sure the drill does not inadvertently puncture the tissue under the nail.

U.S. Pat. No. 5,645,554 attempts to provide depth controlling means so that the drill does not inadvertently puncture the tissue under the nail. The depth controlling means is a tube which is added to a standard drill bit. It is placed around the bit and has an internal circular side wall, which is engaged with one or more flutes of the drill. The enables the tube to move longitudinally along the drill as the tube rotates on the drill.

SUMMARY OF THE INVENTION

The present invention seeks to provide an improved fingernail drill capable of boring a small hole in a nail to relieve blood pressure thereunder, wherein the drill has a built-in stop, such as a shoulder formed near the drill tip, which provides safe penetration depth control so that the user can drill with confidence and safety. The drill is very inexpensive to manufacture and can be used by any person having simple manual manipulation skills.

As will be described below, the fingernail drill can be a flat drill bit (which can be mounted in a rotatable shaft) that has an abutment formed therein or formed by an end of the shaft, or a standard twist drill bit that has an abutment formed in the drill bit, or a standard gun barrel drill bit that has an abutment formed in the drill bit.

There is thus provided in accordance with a non-limiting embodiment of the present invention a fingernail drill including a drill bit and a tip which is capable of drilling through a thickness of a fingernail, wherein the tip extends longitudinally outwards from an abutment integrally formed with the drill bit, and wherein the drill cannot drill past the abutment, and wherein a distance from the abutment to a distal end of the tip is such that the drill can drill through the thickness of the fingernail but cannot damage tissue under the fingernail.

In accordance with an embodiment of the present invention the drill bit extends from a distal end of a shaft, and a proximal end of the shaft is rotatably attached to a finger-rest member.

In accordance with an embodiment of the present invention the drill bit has a width and thickness and the thickness is significantly less than the width. The drill bit may be non-fluted or fluted. The tip may be formed by two arcuate portions that meet at a sharp distal end of the tip, wherein proximal ends of the arcuate portions form part of the abutment. In another embodiment the abutment may include one or more shoulders that adjoin the drill bit. In another embodiment the abutment includes one or more shoulders that extend outwards from the drill bit. In another embodiment the drill bit may have relatively narrow side edges extending from relatively wide flat sides, and the side edges are not perpendicular to the flat sides.

There is also provided in accordance with an embodiment of the present invention a fingernail drill including a drill bit that extends from a distal end of a shaft, a proximal end of the shaft being rotatably attached to a finger-rest member and the distal end including an abutment, the drill bit including a tip which is capable of drilling through a thickness of a fingernail, and wherein the drill cannot drill past the abutment, and wherein a distance from the abutment to a distal end of the tip is such that the drill can drill through the thickness of the fingernail but cannot damage tissue under the fingernail.

BRIEF DESCRIPTION OF THE DRAWINGS

The present invention will be understood and appreciated more fully from the following detailed description, taken in conjunction with the drawings in which:

FIGS. 14-16 are simplified illustrations of the drill bit, showing that the tip of the drill bit has side edges which are not perpendicular to the flat sides of the drill bit so that the drill bit bites and drills easily and properly into a fingernail (the drill bit has standard relief angles for cutting tools), in accordance with different embodiments of the invention, wherein

FIGS. 17-18A are simplified illustrations of a dispenser (syringe) with a distal sealing element (O-ring), constructed and operative in accordance with an embodiment of the invention, wherein

FIGS. 19-20A are simplified illustrations of a dispenser (syringe) with a distal sealing element (sealing sleeve), constructed and operative in accordance with an embodiment of the invention, wherein FIGS. 21-22A are simplified illustrations of a dispenser (pressable tube) with a distal sealing element (elastomeric seal or pad), constructed and operative in accordance with an embodiment of the invention, wherein

DETAILED DESCRIPTION OF EMBODIMENTS

Reference is now made to FIGS. 1-5, which illustrate a fingernail drill 10, constructed and operative in accordance with a non-limiting embodiment of the invention.

Figures 7, 9:
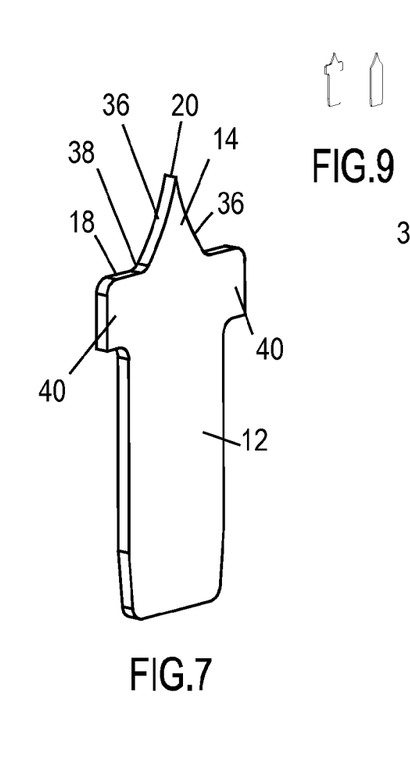
FIG. 7 is a simplified, enlarged pictorial illustration of a drill bit for the fingernail drill of FIG. 5, in accordance with an embodiment of the invention.
FIG. 9 is a simplified, real-size pictorial illustration of the drill bits of FIGS. 7 and 8.

Fingernail drill 10 includes a drill bit 12, one example of which is shown clearly in FIG. 7. As seen in FIG. 7, drill bit 12 has a width and thickness and the thickness is significantly less than the width. In this embodiment, drill bit 12 is non-fluted. Drill bit 12 can be easily and inexpensively manufactured from cold-rolled hard stainless steel or other materials, such as by stamping. (It is noted that stamping is not used for manufacturing prior art drills.) Drill bit is a kind of spade bit but with no spurs at the outer edges. Because of the very low price of the drill bit (e.g., a few cents), the drill can even be provided in sterile packaging for one time use and discarded after use, and thus can be provided in any first aid kit.

Figure 1:
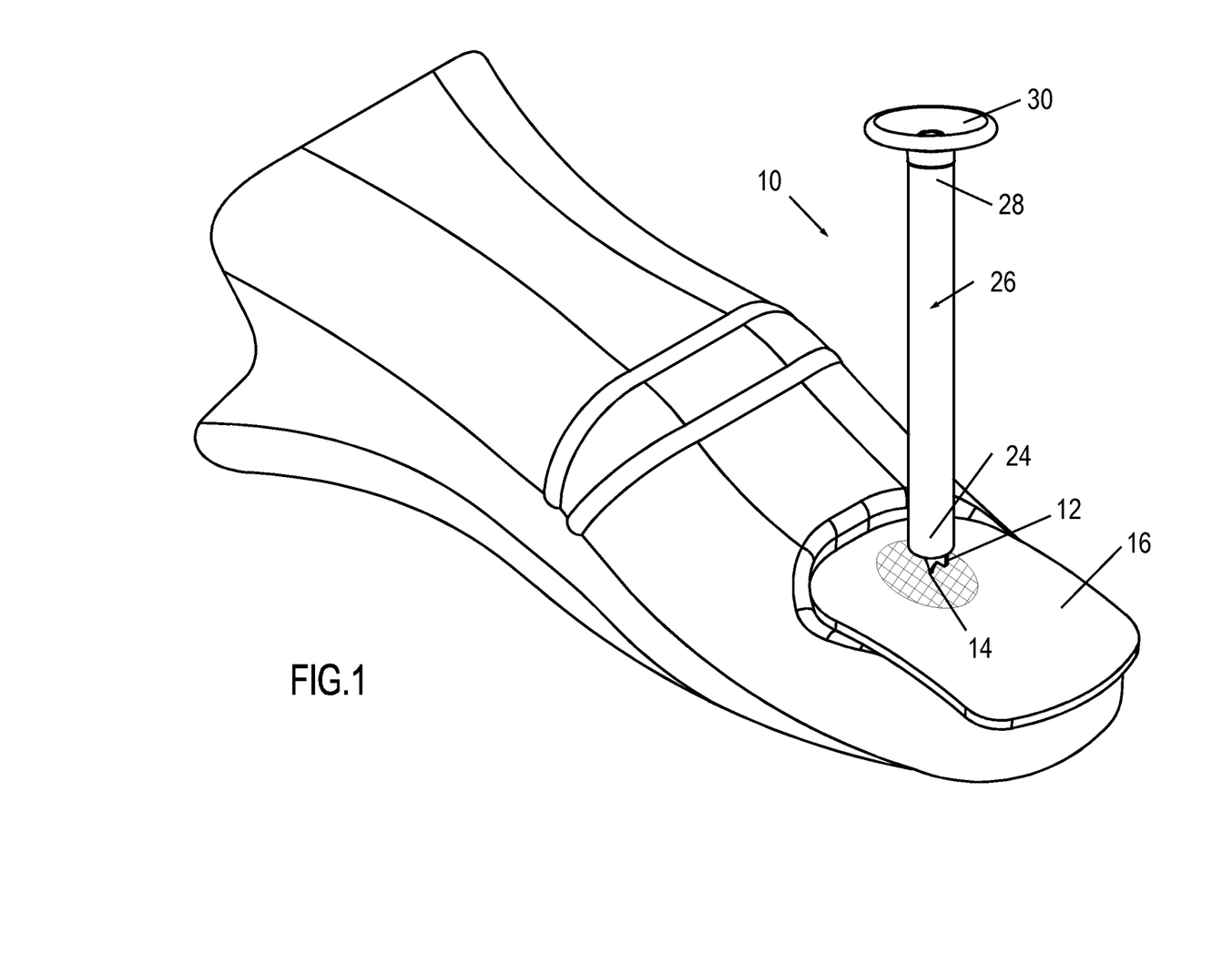
FIG. 1 is a simplified pictorial illustration of a fingernail drill, constructed and operative in accordance with an embodiment of the invention, being used on a thumb.
Figure 2:
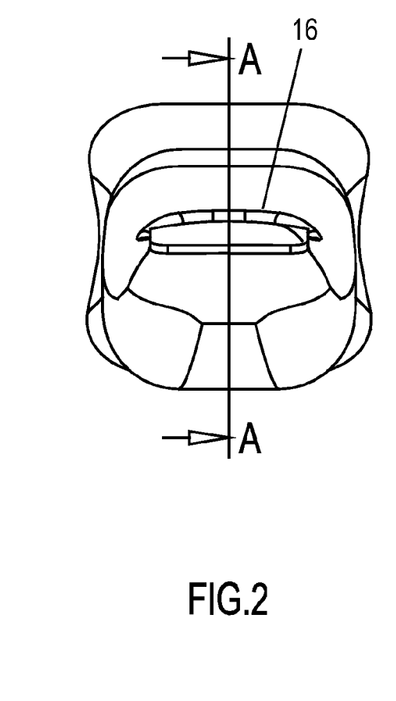
FIG. 2 is a simplified front view of the fingernail, not showing the drill.
Figures 3, 4:
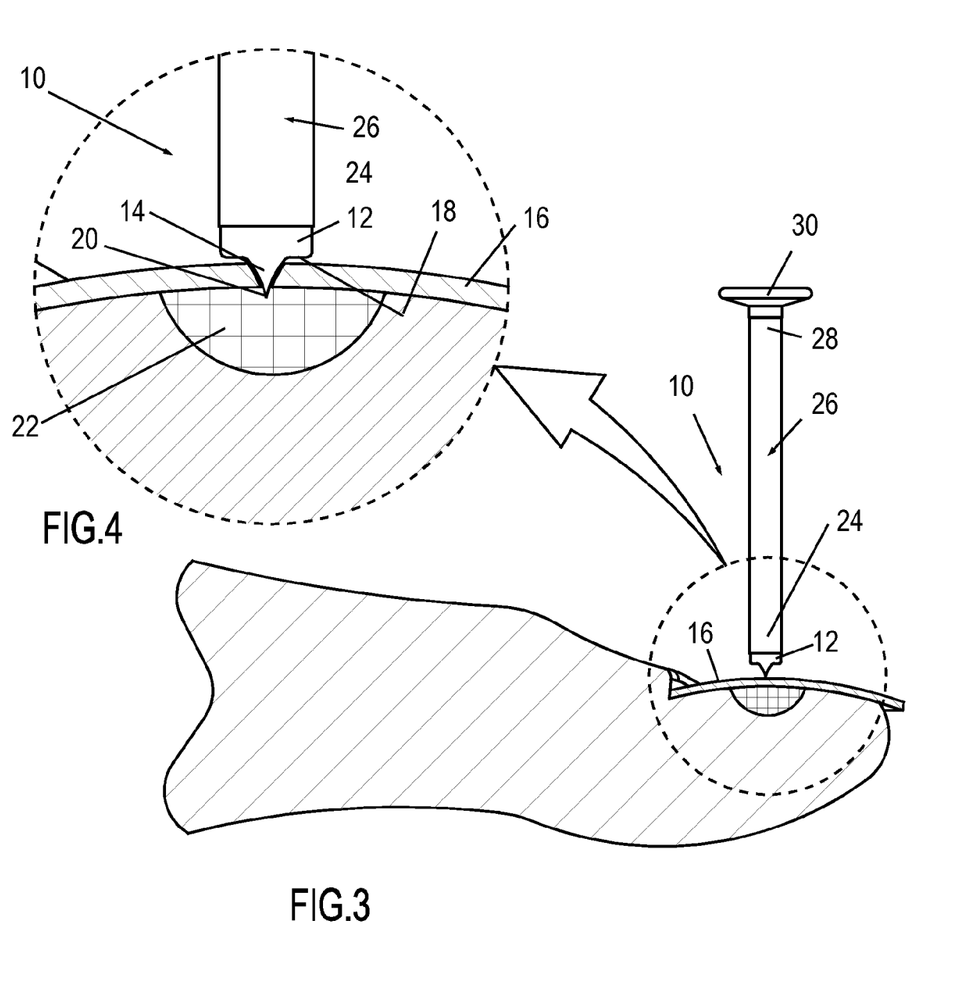
FIG. 3 is a simplified sectional illustration of the finger nail drill on a fingernail, taken along lines A-A in FIG. 2.
FIG. 4 is an enlarged portion of FIG. 3.
Figure 5:
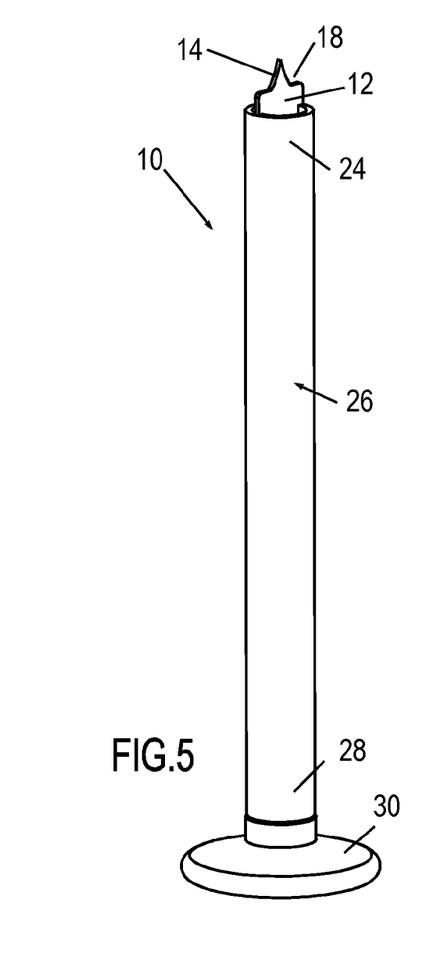
FIG. 5 is a simplified pictorial illustration of the fingernail drill of FIG. 1.

Drill bit 12 has a tip 14 which is capable of drilling through a thickness of a fingernail 16. The tip 14 extends longitudinally outwards from an abutment 18 (FIGS. 4 and 7) integrally formed with drill bit 12. Drill 10 cannot drill past abutment 18. The distance from abutment 18 to a distal end 20 (FIG. 4) of tip 14 is such that drill 10 can drill through the thickness of the fingernail 16 but cannot damage tissue under the fingernail 16. As seen in FIG. 4, the distal end 20 of tip 14 protrudes into a subungual hematoma 22 to drain fluid and relieve pressure.

It is known that there is a variety of thicknesses of fingernails, not just among different people of the population, but even the thicknesses of different fingernails and toenails of one individual varies from thinner to thicker. The distance from abutment 18 to distal end 20 of tip 14 is such that drill 10 can drill through the thickness of the thickest fingernail 16 of a given range of fingernails and yet cannot damage tissue even under the thinnest fingernail of that given range of fingernails. The reason is that when the drill bit tip drills through the fingernail into the subungual hematoma, the subungual hematoma pushes the tissue below it away from the drill bit tip, thereby protecting the tissue from damage by the tip even when the drill is used for the thinnest fingernail of the range.

In accordance with an embodiment of the present invention, drill bit 12 extends from a distal end 24 of a shaft 26 (FIGS. 1, 3, 4 and 5). A proximal end 28 of shaft 26 is rotatably attached to a finger-rest member 30 (FIGS. 1, 3 and 5), similarly to a watchmaker's screwdriver. Drill 10 is used like a watchmaker's screwdriver; the user puts one finger (generally the index finger) on finger-rest member 30 and grasps and turns shaft 26 with two other fingers (generally the thumb and the middle finger). By turning shaft 26, drill bit 12 drills into the fingernail.

Figures 14, 15, 16:
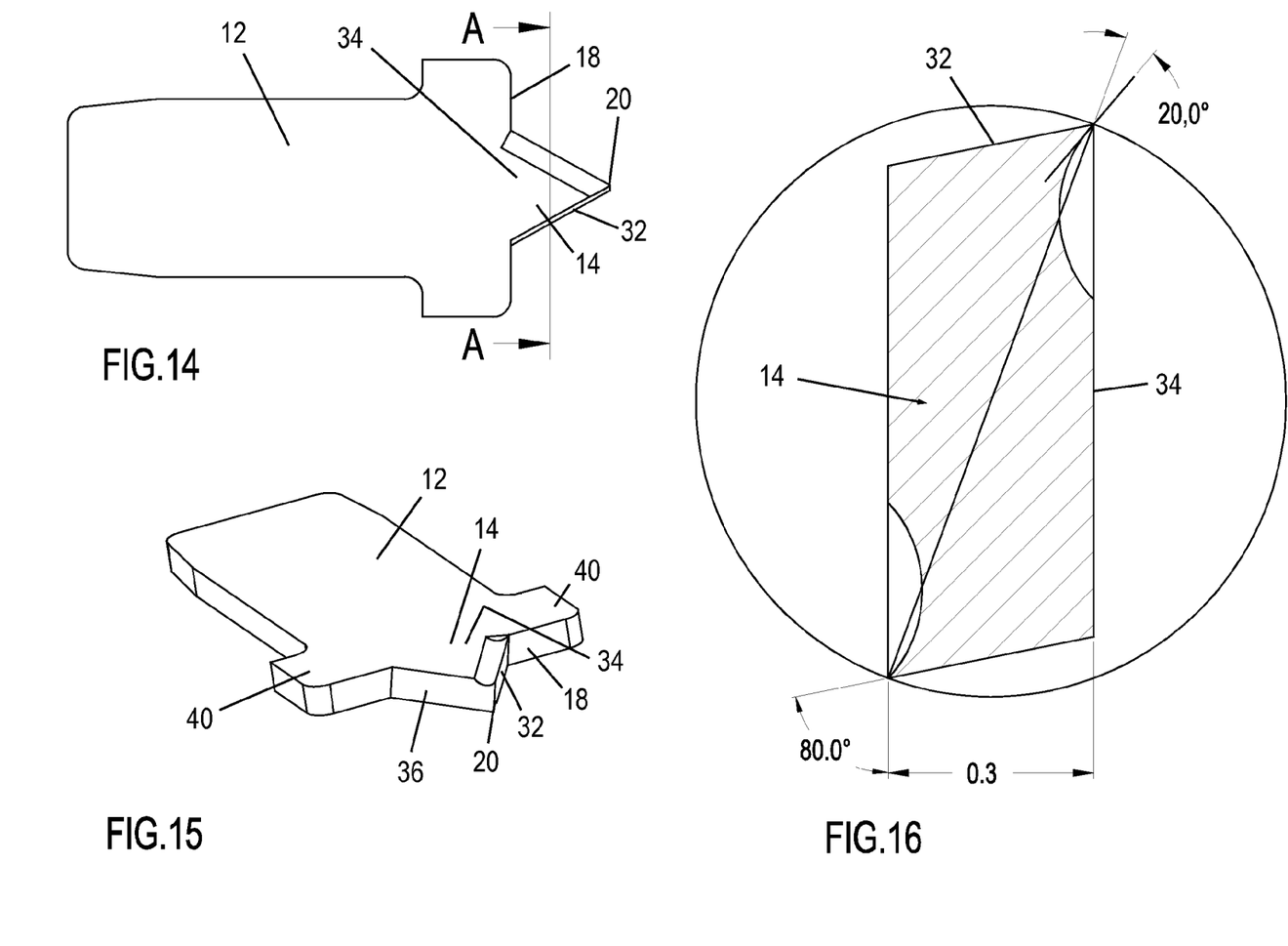
FIG. 14 is a plan view showing the flat side of the drill bit.
FIG. 15 is a perspective view of the drill bit and FIG. 16 is a section view of the drill bit tip, taken along lines A-A in FIG. 14.

Reference is now made to FIGS. 14-16, which illustrate further features of an embodiment of the drill bit 12. It is seen that tip 14 of drill bit 12 has side edges 32 which are not perpendicular (for example, without limitation, about 80° or any standard relief angles for cutting tools) to flat sides 34 of drill bit 12. In this manner, drill bit 12 bites and drills easily and properly into the fingernail.

As seen in FIGS. 7, 14 and 15, tip 14 is formed by two arcuate portions 36 that meet at the sharp distal end 20 of tip 14. Proximal ends 38 of arcuate portions 36 form part of abutment 18. It is noted that abutment 18. In all embodiments of the invention, does not cut because it has no cutting edge. In this embodiment, abutment 18 includes one or more shoulders 40 that adjoin the drill bit 12. Shoulders 40 extend outwards from drill bit 12.

Figure 6:
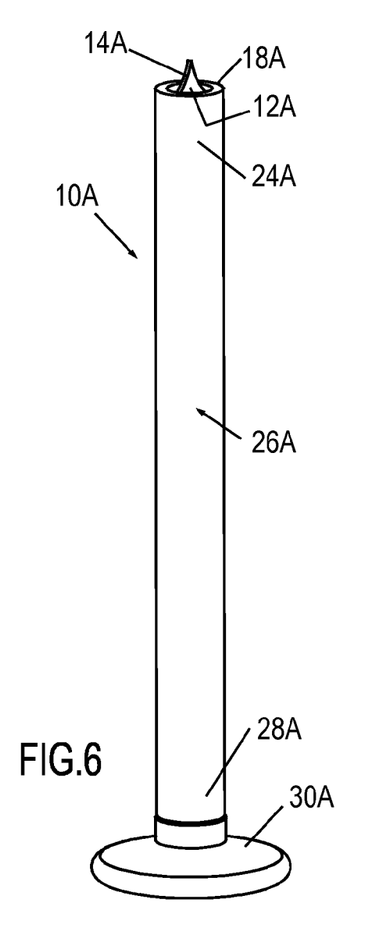
FIG. 6 is a simplified illustration of a fingernail drill, constructed and operative in accordance with another embodiment of the invention.
Figure 8:
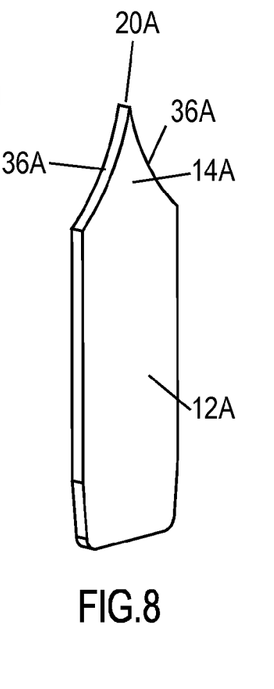
FIG. 8 is a simplified, enlarged pictorial illustration of a drill bit for the fingernail drill of FIG. 6, in accordance with an embodiment of the invention.

Reference is now made to FIGS. 6 and 8, which illustrate another fingernail drill 10A. In this embodiment, as seen in FIG. 8, a drill bit 12A has a thickness significantly less than its width, and is non-fluted, as similarly described for drill bit 12. Also in similarity with drill bit 12, a tip 14A is formed by two arcuate portions 36A that meet at a sharp distal end 20A of tip 14A. (The tip of the drill bit in this and other embodiments can alternatively be formed by straight portions.) Further in similarity with drill bit 12, as seen in FIG. 6, drill bit 12A extends from a distal end 24A of a shaft 26A, and a proximal end 28A of shaft 26A is rotatably attached to a finger-rest member 30A. The distal end 24A of shaft 26A includes an abutment 18A (the distal face of shaft 26A). Thus, in this embodiment, the shaft is the abutment, not the drill bit as in drill 10.

Reference is now made to FIGS. 10-13, which illustrate fingernail drills, constructed and operative in accordance with different embodiments of the invention.

Figure 10:
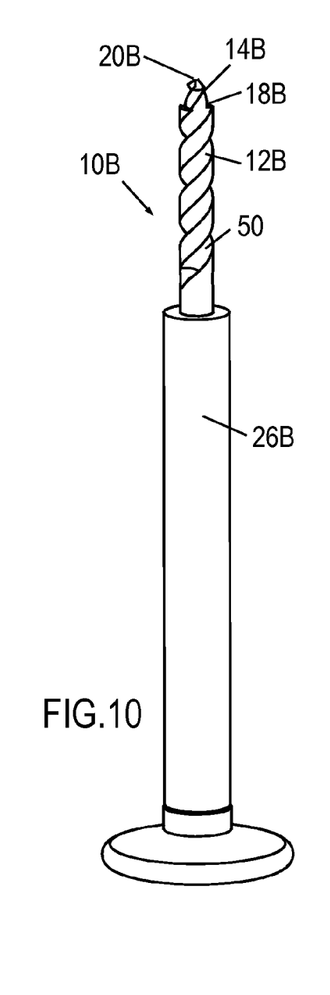
FIGS. 10-13 are simplified illustrations of fingernail drills, constructed and operative in accordance with different embodiments of the invention.

In a fingernail drill 10B of FIG. 10, a drill bit 12B is in the form of a standard twist drill with helical flutes 50. An abutment 18B is machined or otherwise formed near the distal end of drill bit 12B. The abutment 18B is proximal to a distal end 20B of a tip 14B of drill bit 12B such that drill 10B can drill through the thickness of the fingernail but cannot damage tissue under the fingernail. The drill bit 12B is journaled in a shaft 26B, similarly to that described for the embodiment of FIG. 1.

Figure 11:
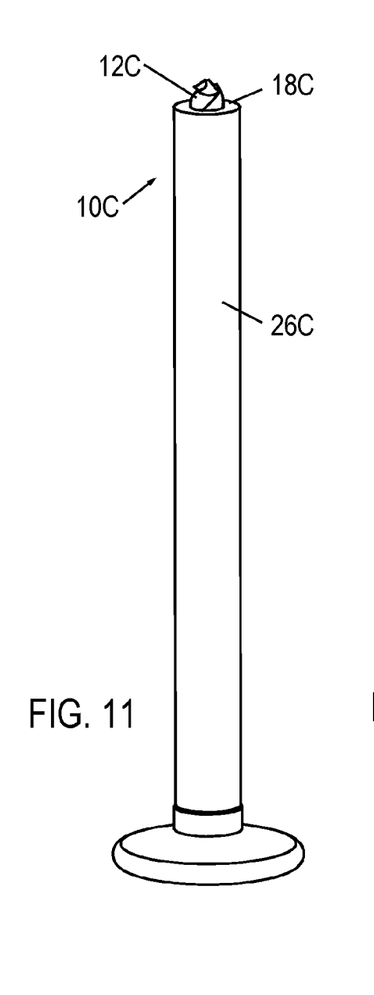

In FIG. 11, a fingernail drill 10C is shown, which is similar to drill 10B of FIG. 10, except that the abutment 18C in this embodiment is the distal end of shaft 26C, as similarly described for the embodiment of FIG. 6. Drill bit 12C does not have an abutment formed in it.

Figure 12:
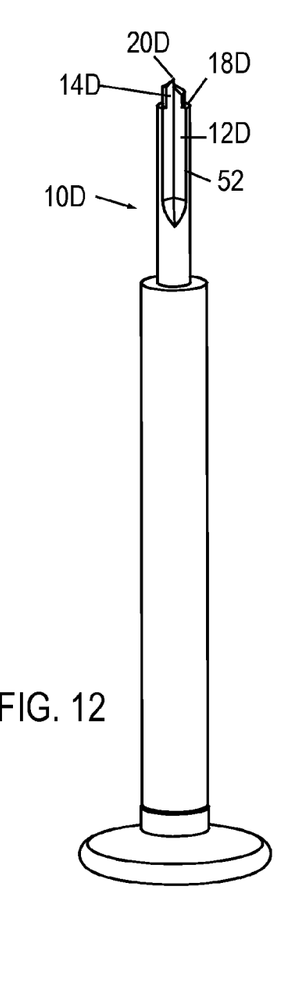

In FIG. 12, a fingernail drill 10D is shown, which is similar to drill 10B of FIG. 10, except that it is in the form of a gun barrel drill bit in which straight flutes 52 are used. Again, an abutment 18D is machined or otherwise formed near the distal end of drill bit 12D. The abutment 18D is proximal to a distal end 20D of a tip 14D of drill bit 12D. Tip 14D is formed from two staggered flutes 52.

Figure 13:
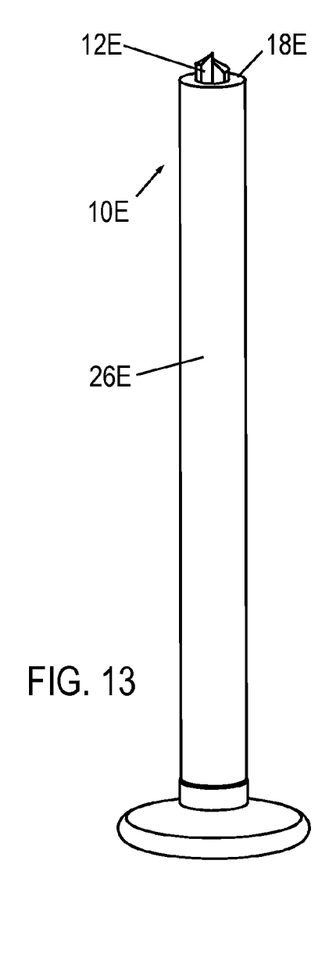

In FIG. 13, a fingernail drill 10E is shown, which is similar to drill 10D of FIG. 12, except that the abutment 18E in this embodiment is the distal end of shaft 26E, as similarly described for the embodiment of FIG. 6. Drill bit 12E does not have an abutment formed in it.

After using any of the drill bits of the invention to drill a hole in the fingernail, a substance (e.g., drug, medicament, etc., the terms being used interchangeably, in any form, such as liquid or thixotropic substance) may be delivered via the hole to tissue in the finger, such as for treating fungus or infections. The invention provides a kit including any of the drills of the invention plus a dispenser for easy introduction of the substance through the hole. Examples of dispensers in accordance with embodiments of the invention are now described.

Figures 17, 18, 18A:
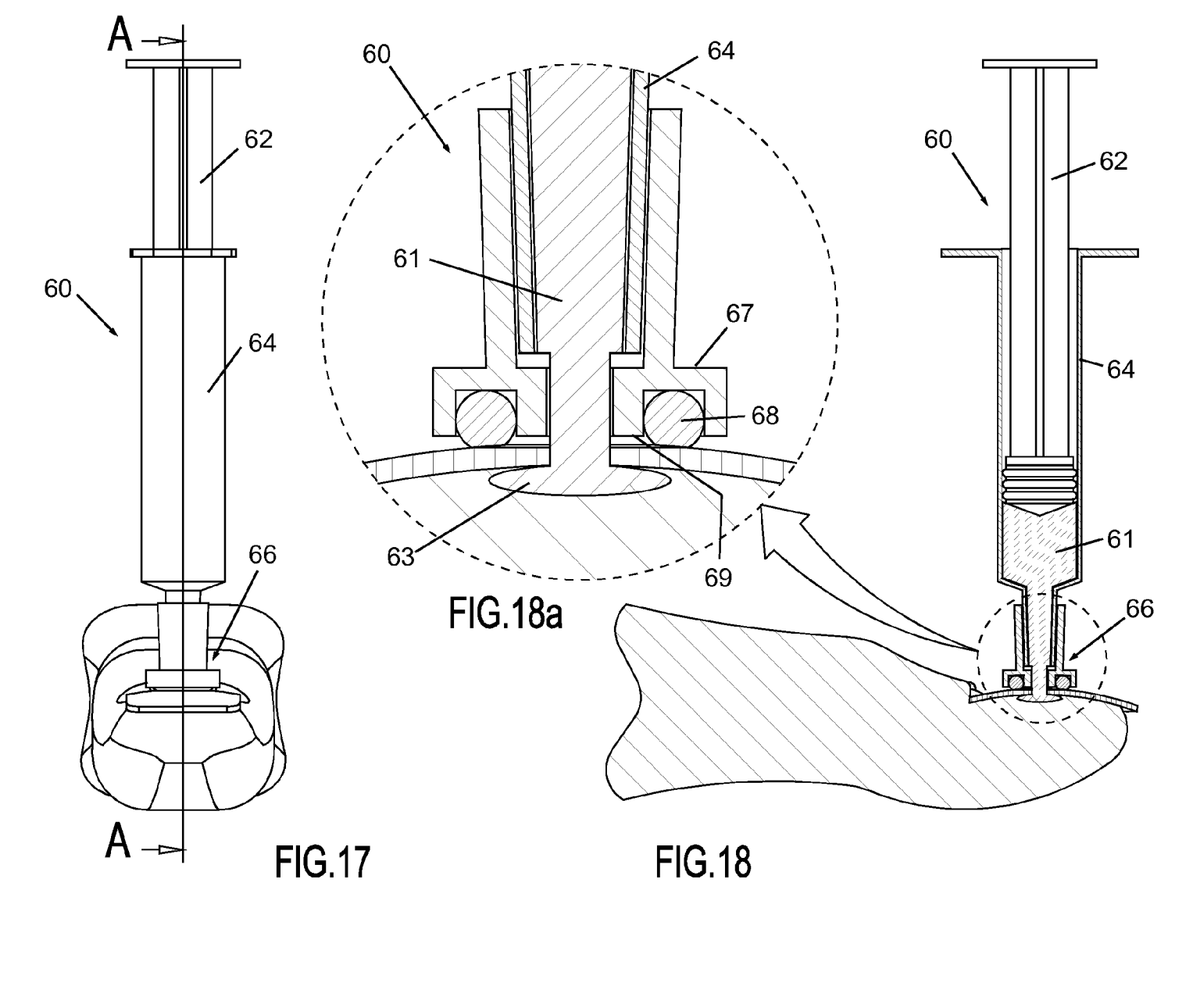
FIG. 17 is a plan view showing the syringe positioned on a fingernail for dispensing a substance through a hole, preferably drilled with any of the drill bits of the invention.
FIG. 18 is a section view of the syringe, taken along lines A-A in FIG. 17.
FIG. 18A is an enlargement of a portion of FIG. 18.

Reference is now made to FIGS. 17-18A, which illustrate a dispenser 60, constructed and operative in accordance with an embodiment of the invention. Dispenser 60 is a syringe with a plunger 62 that slides in a body 64. Dispenser 60 includes a distal sealing element (also referred to as an adaptor) 66, which includes a seal housing 67, which may either be attached to the distal end of body 64 or may be integrally formed therewith. Seal housing 67 includes a seal (O-ring) 68 that is mounted to seal a tissue-facing surface 69 of seal housing 67. The tissue-facing surface 69 is the distal-most surface that faces the fingernail or other body tissue through which it is desired to administer a substance 61 by means of dispenser 60. It is noted that tissue-facing surface 69 does not necessarily have to contact the body tissue. The seal 68 may protrude distally outwards from tissue-facing surface 69. As seen in the figures, plunger 62 pushes out substance 61 from dispenser 60 into a volume 63 (FIG. 18A) of tissue below the fingernail through the hole drilled by the drill of the invention.

Figures 19, 20, 20A:
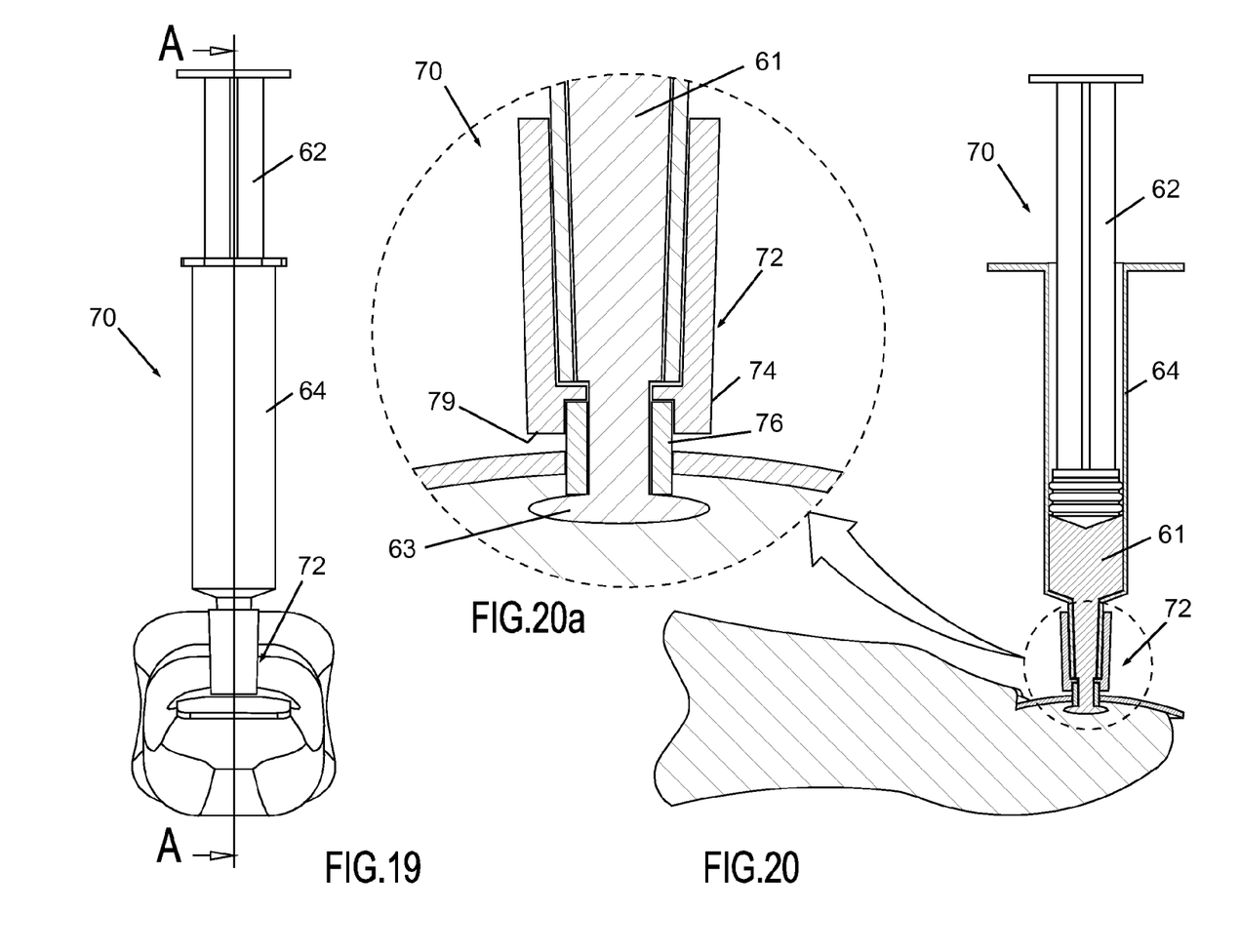
FIG. 19 is a plan view showing the syringe positioned on a fingernail for dispensing a substance through a hole, preferably drilled with any of the drill bits of the invention.
FIG. 20 is a section view of the syringe, taken along lines A-A in FIG. 19.
FIG. 20A is an enlargement of a portion of FIG. 20.

Reference is now made to FIGS. 19-20A, which illustrate a dispenser 70, similar to dispenser 60, except with a different distal sealing element 72. As before, sealing element 72 includes a seal housing 74, which may either be attached to the distal end of body 64 or may be integrally formed therewith. Seal housing 74 includes a sealing sleeve 76 that is mounted to seal a tissue-facing surface 79 of seal housing 74. Sealing sleeve 76 is preferably, but not necessarily, made of an elastomeric material; it can also be made of plastic or even metal. Unlike the 0-ring of the embodiment of FIG. 18A, sealing sleeve 76 not only protrudes distally outwards from tissue-facing surface 79 but also enters the hole that has been drilled by the drill bit, as seen in FIG. 20A. Sealing sleeve 76 may be tapered so that it is slightly less in diameter at its distal tip.

Figures 21, 22, 22A:
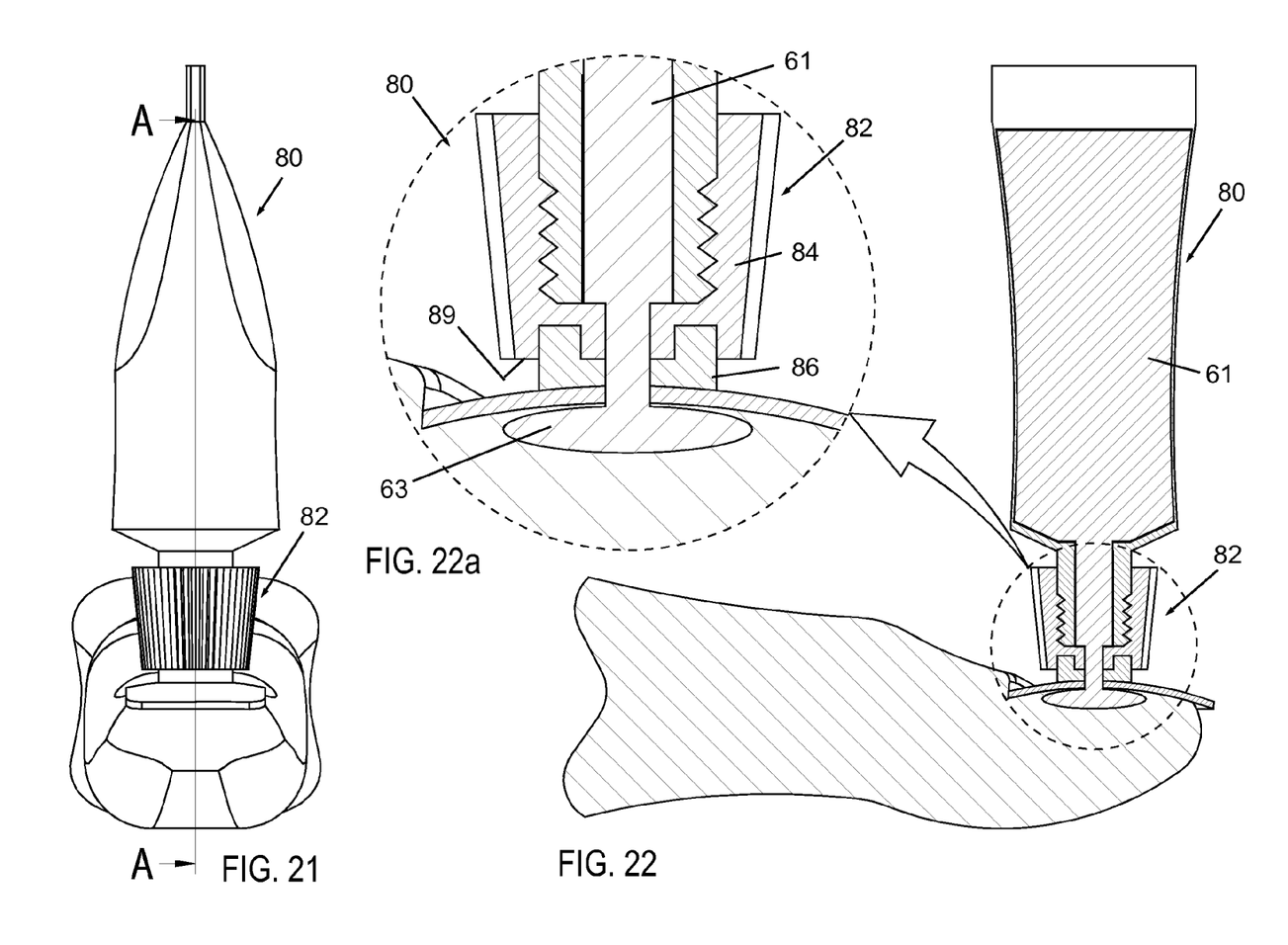
FIG. 21 is a plan view showing the tube positioned on a fingernail for dispensing a substance through a hole, preferably drilled with any of the drill bits of the invention.
FIG. 22 is a section view of the tube, taken along lines A-A in FIG. 21.
FIG. 22A is an enlargement of a portion of FIG. 22.

Reference is now made to FIGS. 21-22A, which illustrate a dispenser 80 which is a pressable tube, such as, but not limited to, a toothpaste-type tube or pasty-type tube for extruding or squeezing substance 61 out of the tube. Dispenser 80 includes a distal sealing element 82, which includes a seal housing 84 that is attached (such as by threaded engagement) to the distal end of the tube. Seal housing 84 includes an elastomeric seal or pad 86 that is mounted to seal a tissue-facing surface 89 of seal housing 84. Seal housing 84 and elastomeric seal 86 may be molded as one piece or two pieces which are assembled together.

What is claimed is:

1. A device comprising:
a fingernail drill comprising a drill bit and a tip which is capable of drilling through a thickness of a fingernail, wherein said tip extends longitudinally outwards from an abutment integrally formed with said drill bit, and wherein said drill cannot drill past said abutment, and wherein a distance from said abutment to a distal end of said tip is such that said drill can drill through the thickness of the fingernail but cannot damage tissue under the fingernail, and wherein said drill bit extends from a distal end of a shaft, and a proximal end of said shaft is rotatably attached to a finger-rest member, and wherein said tip formed by two acruate portions that meet at a sharp distal end of said tip, and wherein proximal ends of said acruate portions form part of said abutment.

2. The device according to claim 1, wherein said drill bit has a width and thickness and the thickness is significantly less than the width.

3. The device according to claim 1, wherein said drill bit is non-fluted.

4. The device according to claim 1, wherein said drill bit is fluted.

5. The device according to claim 1, wherein said shaft is located between said finger-rest member and said tip.

6. The device according to claim 1, wherein said abutment comprises one or more shoulders that adjoin said drill bit.

7. The device according to claim 1, wherein said abutment comprises one or more shoulders that extend outwards from said drill bit.

8. The device according to claim 1, wherein said drill bit has relatively narrow side edges extending from relatively wide flat sides, and said side edges are not perpendicular to said flat sides.

9. The device according to claim 1, further comprising a dispenser for dispensing a substance through a hole drilled by said fingernail drill.

10. The device according to claim 9, wherein said dispenser comprises a distal sealing element, which comprises a seal housing disposed on a distal end of said dispenser, and wherein said seal housing comprises a seal that is mounted to seal a tissue-facing surface of said seal housing.

* * * * *